(12) United States Patent
Gambale et al.

(10) Patent No.: US 6,440,136 B1
(45) Date of Patent: Aug. 27, 2002

(54) APPARATUS FOR ATTACHING TO BONE

(75) Inventors: Michael A. Gambale, Hingham, MA (US); James M. Kuras, Macedonia; Charles Fredrick Birchall, Jr., Mentor, both of OH (US)

(73) Assignee: Medtronic PS Medical, Inc., Goleta, CA (US)

( * ) Notice: Subject to any disclaimer, the term of this patent is extended or adjusted under 35 U.S.C. 154(b) by 0 days.

(21) Appl. No.: 09/577,767

(22) Filed: May 24, 2000

(51) Int. Cl.[7] .............................................. A61B 17/86
(52) U.S. Cl. ........................ 606/73; 606/104; 411/402
(58) Field of Search .............................. 606/60, 65, 66, 606/72, 73, 232; 411/402, 403, 404, 405, 407, 408

(56) References Cited

U.S. PATENT DOCUMENTS

| | | | |
|---|---|---|---|
| 2,180,633 A | * | 11/1939 | Holt |
| 2,258,326 A | * | 10/1941 | Holt |
| 3,236,141 A | | 2/1966 | Smith |
| 5,169,400 A | | 12/1992 | Muhling et al. |
| 5,423,819 A | | 6/1995 | Small et al. |
| 5,484,440 A | | 1/1996 | Allard |
| 5,645,546 A | | 7/1997 | Fard |
| 5,776,134 A | | 7/1998 | Howland |
| 5,797,914 A | | 8/1998 | Leibinger |
| 5,925,048 A | | 7/1999 | Ahmad et al. |
| 5,928,236 A | | 7/1999 | Augagneur et al. |
| 5,957,927 A | | 9/1999 | Magee et al. |
| 5,961,524 A | | 10/1999 | Crombie |
| 5,971,987 A | | 10/1999 | Huxel et al. |
| 6,149,653 A | * | 11/2000 | Deslauriers ................ 606/72 |

FOREIGN PATENT DOCUMENTS

| | | | |
|---|---|---|---|
| DE | 3701574 | * | 8/1988 |
| GB | 2092253 | * | 8/1982 |

* cited by examiner

Primary Examiner—David O. Reip
(74) Attorney, Agent, or Firm—Tarolli, Sundheim, Covell, Tummino & Szabo L.L.P.

(57) ABSTRACT

An apparatus (10) for attaching to bone comprises a one-piece, homogeneous screw (12) engageable by a driver for driving the screw into bone. The screw (12) has a shaft portion (20) and a head portion (40) extending from the shaft portion. The shaft portion (20) has an outer surface (26) with a thread convolution (28). The head portion (40) includes oppositely disposed first and second axial ends (42 and 44) and a peripheral surface (50) extending between the ends. The first axial end (42) adjoins the shaft portion (20). The second axial end (44) includes an end surface (46). The head portion (40) has a plurality of slots (60) extending axially from the end surface (46) to the first axial end (42). The slots (60) further extend through the peripheral surface (50) of the head portion (40) and radially inward from the peripheral surface of the head portion. In accordance with another feature, the apparatus (10) further comprises a screwdriver (14) for driving the screw (12) into bone (130).

18 Claims, 4 Drawing Sheets

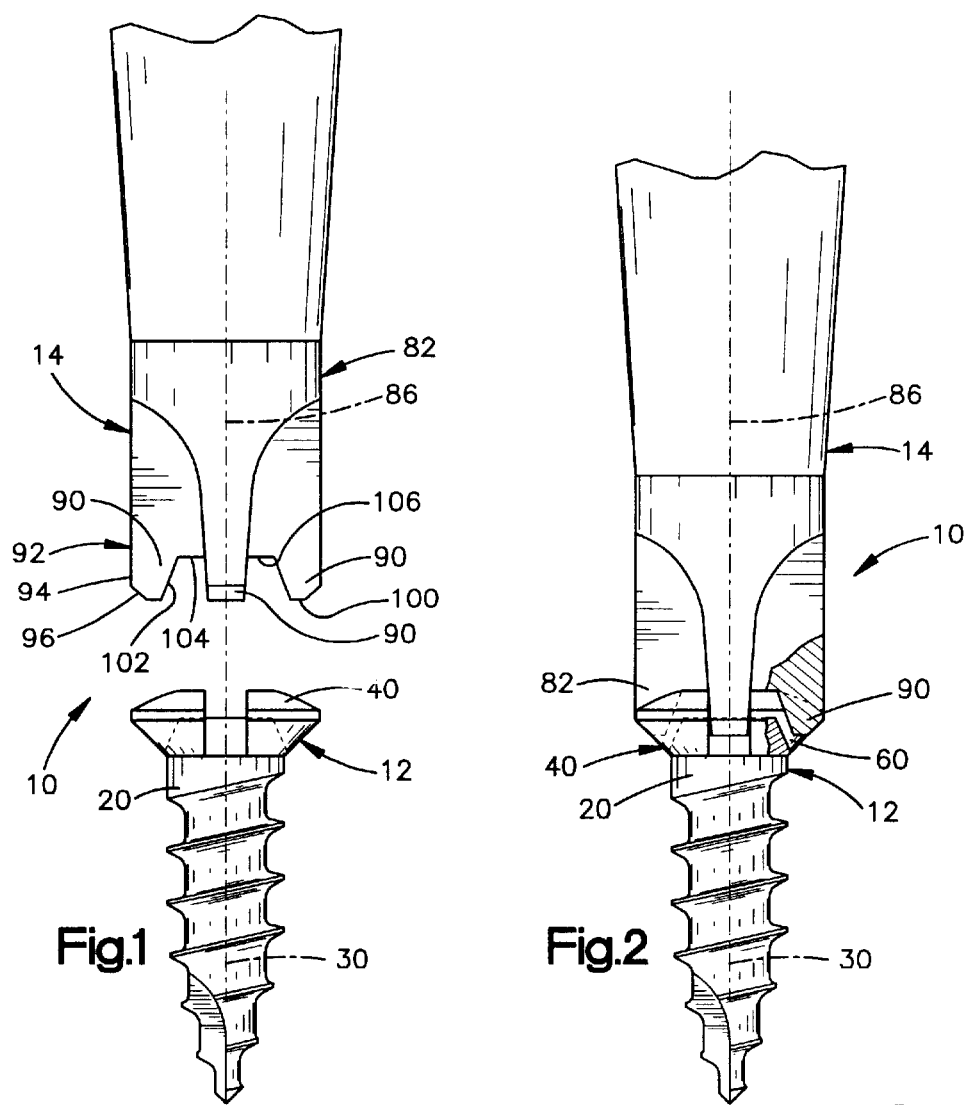
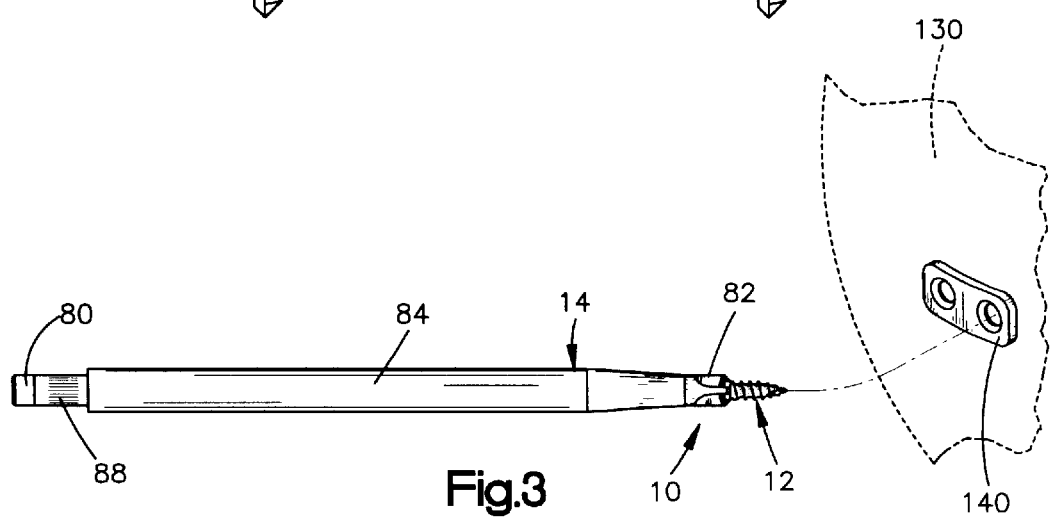

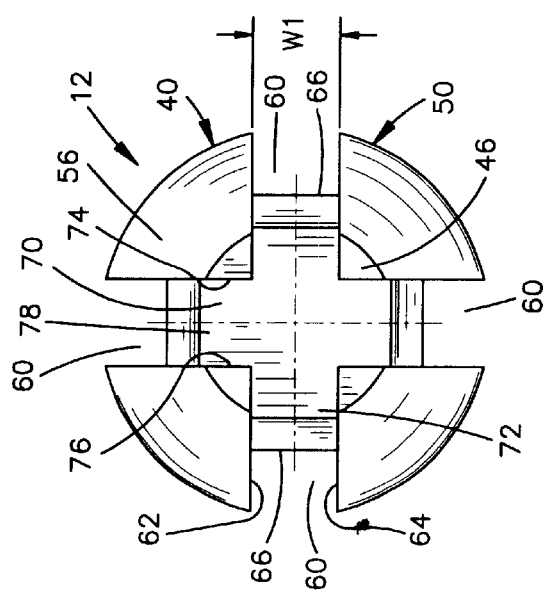
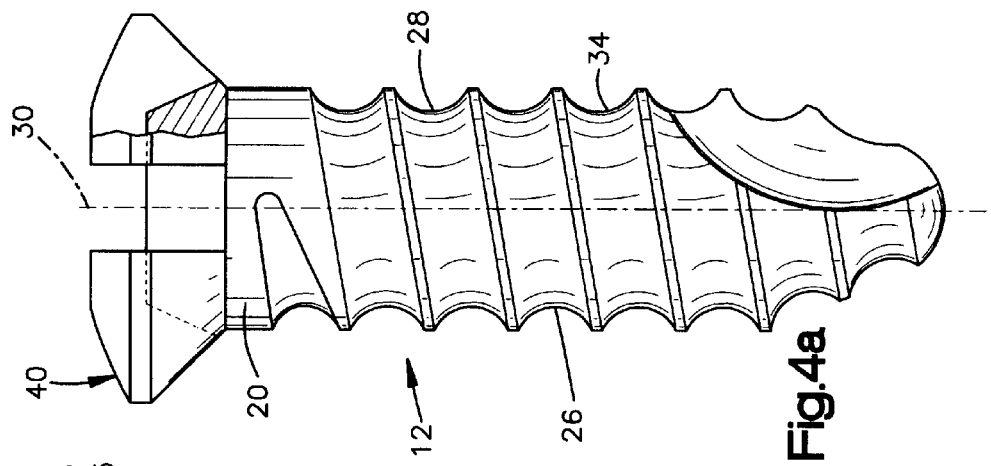
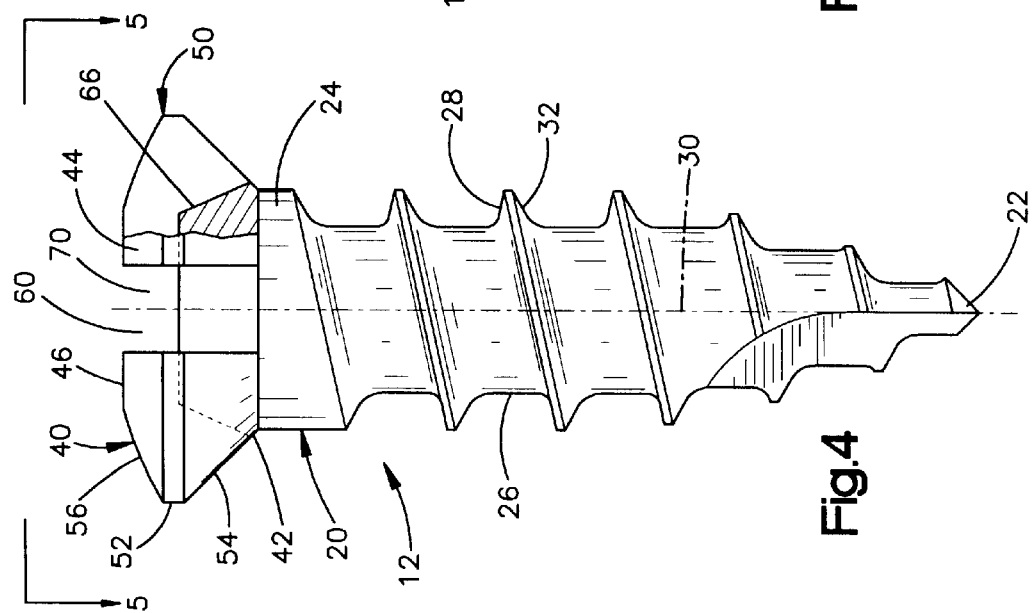

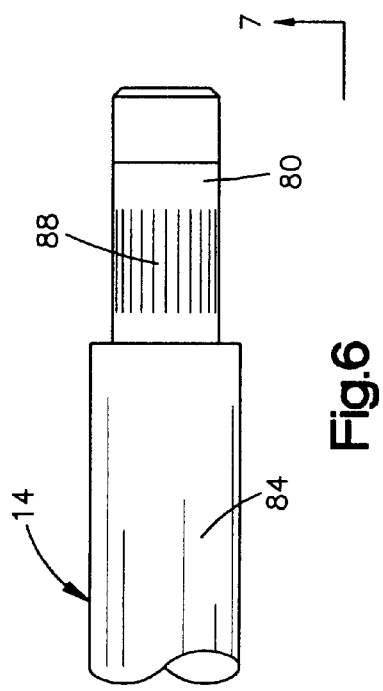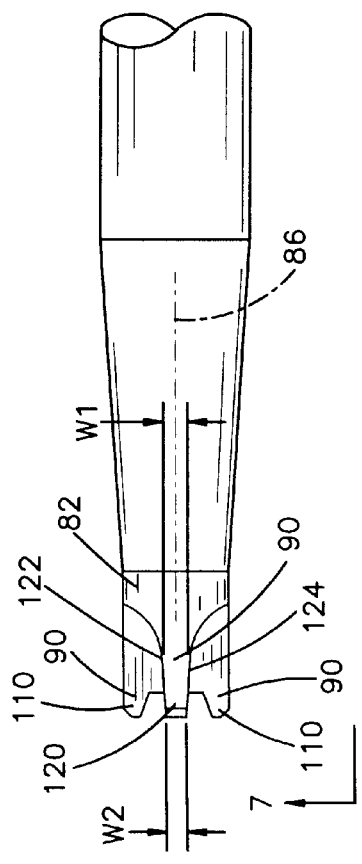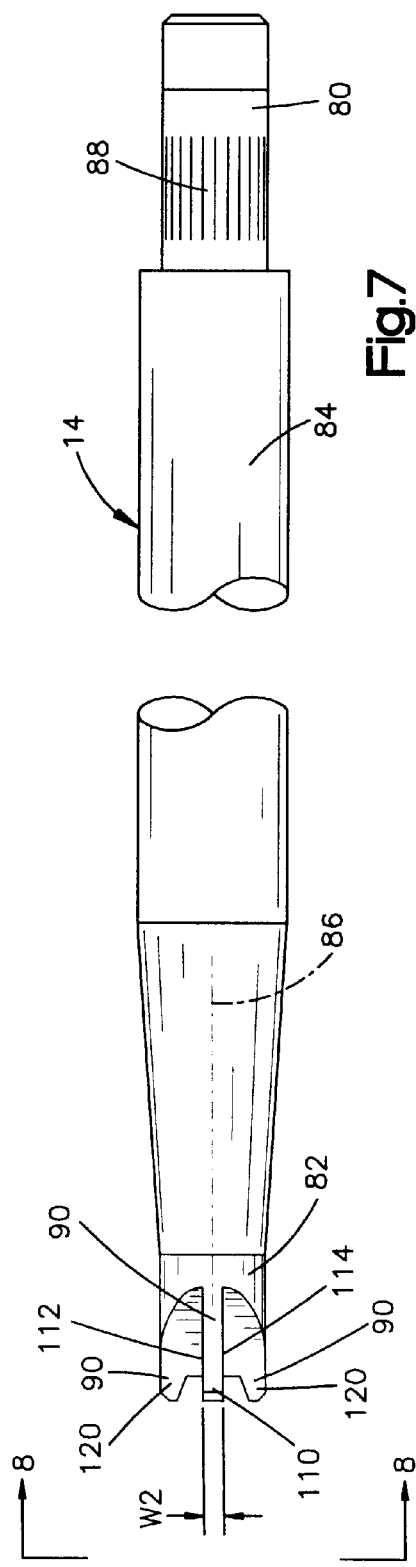

APPARATUS FOR ATTACHING TO BONE

TECHNICAL FIELD

The present invention relates to an apparatus for attaching to bone. More particularly, the present invention is directed to a bone screw and includes an associated screwdriver for driving the screw into bone.

BACKGROUND OF THE INVENTION

Various types of fasteners are known for use in the medical field for attachment to human bone matter. Most of the known fasteners, whether permanent or temporary, are made of a bio-compatible metal, such as titanium or a titanium alloy, or a bio-absorbable material. Many of the commonly used fasteners are self-tapping or self-drilling bone screws. Self-tapping and/or self-drilling bone screws are often used in conjunction with a bio-compatible metal plate, such as in oral or maxillofacial surgery.

Of particular concern in the medical field is the ability of a bone screw to be retained on the end of an associated screwdriver during placement of the screw on the proper location of the bone. This concern arises because frequently the surgeon can only use one hand to pick-up the bone screw and place it in the proper attachment location, and because the relatively small size of such bone screws can make them difficult to work with.

Another concern for bone screws is the ability of the screwdriver to remain engaged with the screw while the screw is being driven into the bone. This concern arises because disengagement of the screwdriver from the screw could result in loss of the screw, or in harmful contact of the screwdriver with adjacent body tissue.

Accordingly, an apparatus for attaching to bone which retains a bone screw on the end of an associated screwdriver during pick-up and placement of the screw, as well as during driving of the screw, is desirable.

SUMMARY OF THE INVENTION

The present invention is an apparatus for attaching to bone. The apparatus comprises a one-piece, homogeneous screw engageable by a driver for driving the screw into bone. The screw has a shaft portion and a head portion extending from the shaft portion. The shaft portion has an outer surface with a thread convolution. The head portion includes oppositely disposed first and second axial ends and a peripheral surface extending between the ends. The first axial end adjoins the shaft portion. The second axial end includes an end surface. The head portion has a plurality of slots extending axially from the end surface to the first axial end. The slots further extend through the peripheral surface of the head portion and radially inward from the peripheral surface of the head portion.

In accordance with another aspect of the present invention, the apparatus further comprises a driver for driving the screw into bone. The driver has an end section with a plurality of blades projecting axially from the end section. Each of the plurality of blades is adapted for receipt in and to drivingly engage a respective one of the slots in the head portion of the screw. Further, each blade has a peripheral surface that corresponds to the shape of the peripheral surface on the head portion of the bone screw.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is an exploded side view of an apparatus constructed in accordance with the present invention;

FIG. 2 is a side view, partly in section, of the apparatus of FIG. 1 in an assembled condition;

FIG. 3 is a side view of the apparatus of FIG. 1 in a representative application;

FIG. 4 is a side view, partly in section, of a component of the apparatus of FIG. 1;

FIG. 4a is a side view similar to FIG. 4 illustrating an alternate embodiment of the present invention;

FIG. 5 is an end view of the component shown in FIG. 4;

FIG. 6 is a side view of another component of the apparatus of FIG. 1;

FIG. 7 is another side view of the component shown in FIG. 6;

DESCRIPTION OF PREFERRED EMBODIMENTS

Figure 8:
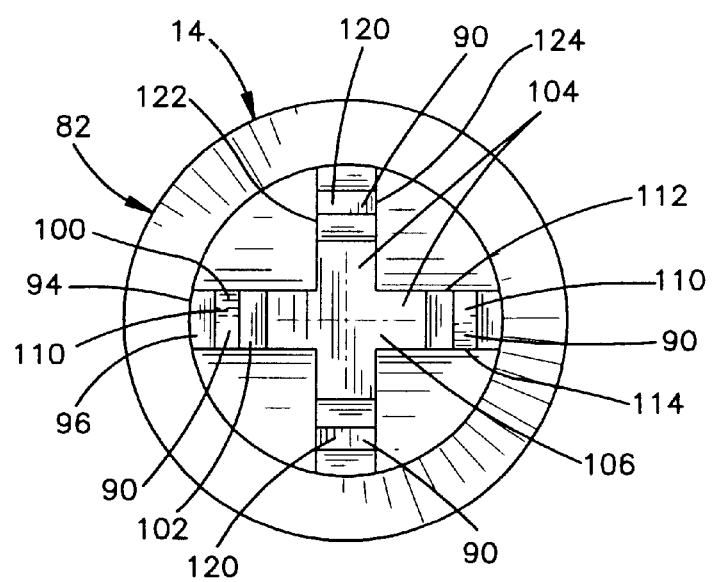
FIG. 8 is an end view of the component shown in FIG. 6.

The present invention relates to an apparatus for attaching to bone material, such as human bone. As representative of the present invention, FIG. 1 illustrates an apparatus 10 comprising a bone screw 12 and a driver 14 for driving the bone screw.

The bone screw 12 is a one-piece component made from a homogeneous, bio-compatible material. Preferably, the screw 12 is made of titanium or a titanium alloy, but it is contemplated that the screw could also be made of a bio-compatible, non-metallic material. The screw 12 has a shaft portion 20 and a head portion 40 that extends from the shaft portion along a first axis 30.

The shaft portion 20 of the bone screw 12 has a distal end 22 and a proximal end 24 that adjoins the head portion 30. The shaft portion 20 includes an outer surface 26 (FIG. 4) with a thread convolution 28. The thread convolution 28 extends axially from the distal end 22 of the shaft portion 20 to the proximal end 24 of the shaft portion. In accordance with one embodiment of the present invention, the thread convolution 28 comprises a self-drilling pattern 32 known in the art. Alternatively, in accordance with another embodiment of the present invention, the thread convolution 28 comprises a self-tapping pattern 34 (FIG. 4a) known in the art.

The head portion 40 of the bone screw 12 includes oppositely disposed first and second axial ends 42 and 44 (FIG. 4). The first axial end 42 of the head portion 40 adjoins the proximal end 24 of the shaft portion 20. The second axial end 44 of the head portion 40 includes a radially extending end surface 46. In the embodiment of FIG. 4, the end surface 46 is generally planar, but it is contemplated that the end surface could instead have an arcuate or convex shape.

A peripheral surface 50 extends circumferentially from the first axial end 42 of the head portion 40 to the end surface 46 at the second axial end 44 of the head portion. The peripheral surface 50 is defined by a first surface portion 52, a second surface portion 54, and a third surface portion 56. The first surface portion 52 is cylindrical in shape. The second surface portion 54 has a conical shape and extends from the first surface portion 52 to the outer surface 26 at the proximal end 24 of the shaft portion 20 of the screw 12. The third surface portion 56 tapers from the first surface portion 52 to the end surface 46. The tapered shape of the third surface portion 56 can be either conical or arcuate.

The head portion 40 of the bone screw 12 further includes a plurality of slots 60 extending axially from the end surface 46 to the first axial end 42 of the head portion. In accordance with the preferred embodiment of the invention, the head portion 40 has four slots 60 spaced 90° apart as may be seen in FIG. 5. Each of the slots 60 extends axially through the first surface portion 52, the second surface portion 54, and through the third surface portion 56 that together define the peripheral surface 50 of the head portion 40. Further, each of the slots 60 extends radially inward from the first surface portion 52, the second surface portion 54, and the third surface portion 56.

Each of the slots 60 in the head portion 40 of the screw 12 is further defined by parallel first and second side walls 62 and 64 (FIG. 5) and an inner wall 66 that connects the first and second side walls. The inner wall 66 is a segment of a frustum that increases in diameter as the inner wall approaches the first axial end 42 of the head portion 40. The inner wall 66 defines a width W1 for each of the slots 60 in the head portion 40.

The head portion 40 of the bone screw 12 further includes intersecting first and second grooves 70 and 72 formed in the end surface 46 at the second axial end 44. The first groove 70 extends radially between a diametrically opposed first pair (not numbered) of the four slots 60 in the head portion 40. Similarly, the second groove 72 extends radially between a diametrically opposed second pair (not numbered) of the four slots 60 in the head portion 40. Each of the first and second grooves 70 and 72 is defined by parallel first and second side walls 74 and 76 and an end wall 78 that connects the side walls. The intersection of the first and second grooves 70 and 72 in the second end portion 44 forms a cross or "plus" symbol that is centered on the first axis 30.

The driver 14 for driving the bone screw 12 comprises a bit for use with a manually graspable handle (not shown) or for insertion into the chuck of a powered tool (not shown). The driver 14 is preferably made from stainless steel, but could alternatively be made of another suitable material. The driver 14 has oppositely disposed first and second end sections 80 and 82 and a generally cylindrical main body portion 84 extending between the end sections along a second axis 86. The first end section 80 of the driver 14 includes a knurled outer surface 88 for mating with the handle or tool mentioned above.

Figure 9:
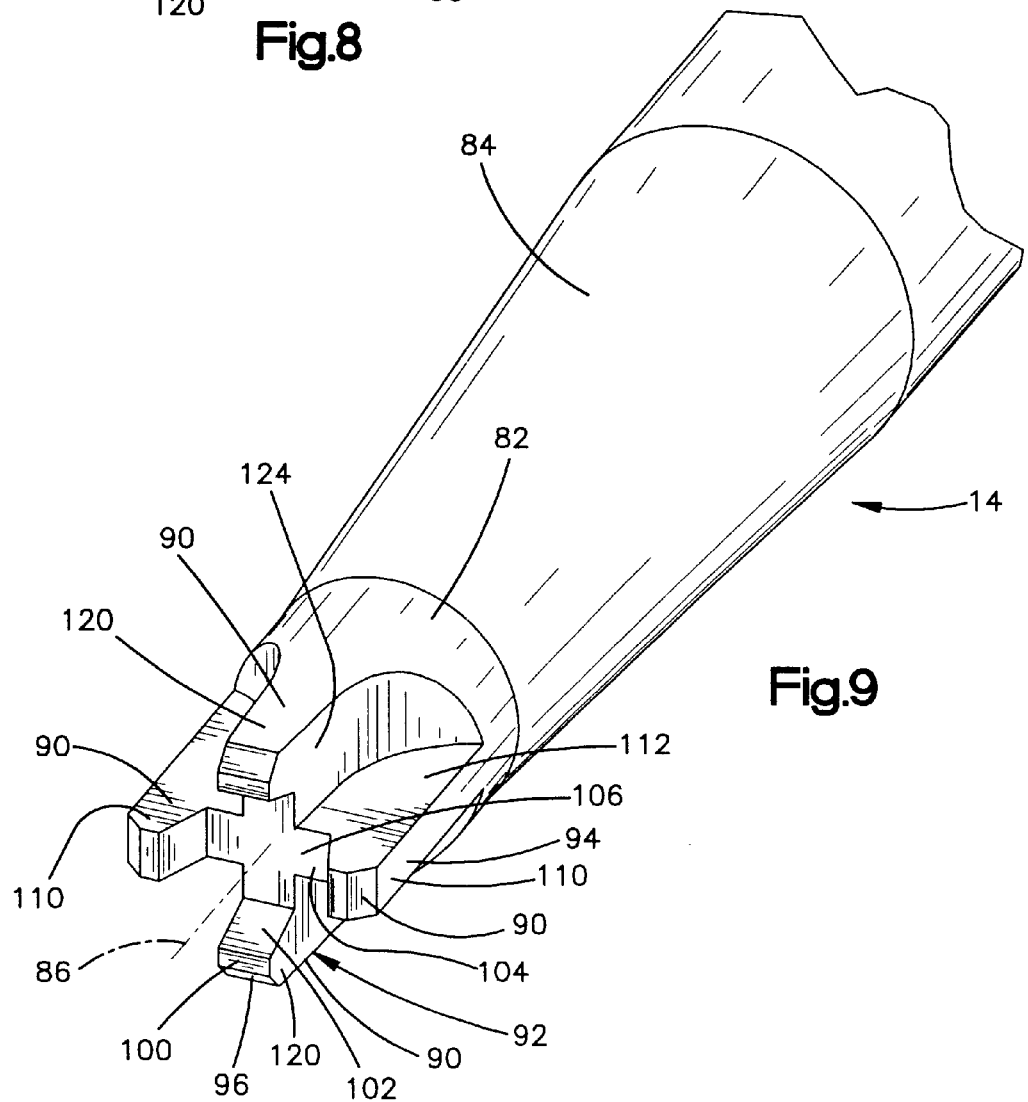
FIG. 9 is a perspective view of a portion of the component shown in FIG. 6.

The second end section 82 of the driver 14 includes a plurality of blades 90 that project axially away from the second end section. In accordance with the preferred embodiment of the invention, the end section 82 has four blades spaced 90° apart as may be seen in FIGS. 8 and 9. The blades 90 are designed to be received in and drivingly engage the slots 60 in the head portion 40 of the bone screw 12 as described further below.

Each of the blades 60 is defined by a peripheral surface 92 (FIG. 1) that corresponds to at least a portion of the peripheral surface 50 on the head portion 40 of the bone screw 12. More specifically, each of the blades 90 includes a cylindrical surface 94 and a chamfered surface 96 that form the peripheral surface 92. The cylindrical surface 94 on each blade 90 has substantially the same diameter as the cylindrical first surface portion 52 of the peripheral surface 90 on the head portion 40 of the bone screw 12. Further, the chamfered surface 96 on each blade 90 extends at substantially the same angle from the cylindrical surface 94 as the second surface portion 54 on the head portion 40 extends from the first surface portion 52.

Each of the blades 90 on the driver 14 further includes a radially extending terminal surface 100, an angled surface 102, and a radially extending stop surface 104. The stop surfaces 104 on the blades 90 join together to form a continuous stop surface 106 shaped like a cross or "plus" symbol centered on the second axis 86. Each of the angled surfaces 102, which extend at approximately the same angle as the inner wall 66 of each of the slots 60 in the head portion 40 of the screw 12, connects the continuous stop surface 104 with a respective one of the terminal surfaces 100.

A diametrically opposed first pair 110 (FIG. 9) of the four blades 90 on the end section 82 of the driver 14 are further defined by parallel first and second side surfaces 112 and 114 (FIG. 7). The side surfaces 112 and 114 are spaced apart by a distance W2 that is slightly less than the width W1 of the slots 60 in the head portion 40 of the screw 12. A diametrically opposed second pair 120 (FIG. 9) of the four blades 90 are further defined by divergent third and fourth surfaces 122 and 124 (FIG. 6). Adjacent the end surface 100 of each of the second pair 120 of blades 90, the side surfaces 122 and 124 are spaced apart by the distance W2. The third and fourth side surfaces 122 and 124 taper away from each other so that, in the proximity of the radial plane of the continuous stop surface 106, the third and fourth side surfaces are spaced apart by a distance approximately equal to the width W1 of the slots 60 in the screw 12.

To use the apparatus 10, the bone screw 12 and the driver 14 are brought into engagement with one another. This is done by manually pushing the head portion 40 of the screw 12 onto the end section 82 of the driver, or vice versa. In accordance with a preferred embodiment of the invention, a number of screws 12 are held in a sterile container (not shown) prior to use, and the end section 82 of the driver 14 is inserted into the head portion 40 of a given screw to remove the screw from the container for attachment to a bone.

More specifically, the bone screw 12 is engaged by the driver 14 by inserting each of the blades 90 on the end section 82 of the driver 14 into a respective one of the slots 60 in the head portion 40. The first pair 110 of blades 90 on the driver 14 slide into a diametrically opposed first pair (not numbered) of the slots 60 with just a small amount of clearance (i.e. the difference between the width W1 of the slots and the width W2 of the blades) between the side walls 62 and 64 of the slots and the side surfaces 112 and 114, respectively of the blades.

The second pair 120 of blades 90 are received in a diametrically opposed second pair (not numbered) of the slots 60 in the head portion 40 of the screw 12. As the blades 90 are pushed axially farther into the slots 60 in the screw 12, the divergent side surfaces 122 and 124 on each of the second pair 120 of blades 90 engage the respective side walls 62 and 64 of one of the slots with an interference fit. The interference fit of the second pair 120 of blades 90 wedges the screw 12 onto the end section 82 of the driver 14 as shown in FIG. 2, which is an illustration of the apparatus 10 when the blades are fully inserted into the slots 60 in the screw. The driver 14 and the attached screw 12 can now be moved to a location where the screw will be attached to a bone, such as the bone 130 illustrated in FIG. 3.

As shown in FIG. 2, when the blades 90 are fully inserted into the slots 60 in the screw 12, the cylindrical surface 94 on each blade lies flush with the first surface portion 52 on the head portion 40 of the screw. Also, the chamfered surface 96 on each blade 90 lies flush with the second surface portion 54 on the screw 12. The correspondence of the aforementioned surfaces prevents the blades 90 from projecting radially or axially out of the slots 60 in the head portion 40 of the bone screw 12 when the bone screw is wedged onto the end section 82 of the driver 14. This is important so that the screw 12 fits properly in the countersunk opening through a metal attachment plate, such as the representative plate 140 (FIG. 3) which can be included as part of the apparatus 10. Further, whether or not an attachment plate is used, it is important that the blades 90 do not project out of the slots 60 where the blades could come into contact with bone or other tissue during rotation of the driver 14.

When positioned in the proper location for attachment to a bone, the bone screw 12 is driven into the bone by rotating the driver 14. As the driver 14 is rotated, a side surface 112 or 122 of each of the four blades 90 bears against a side wall 62 of each of the four slots 60, providing a relatively large amount of total surface area in contact. This large amount of surface area in contact provides for superior torque transmission capability. In addition, the large amount of surface area in contact helps to keep the second axis 86 of the driver 14 aligned with the first axis 30 of the screw 12, thereby reducing off-axis rotation of the driver which could lead to disengagement of the driver from the screw. Further, should the driver 14 begin to wobble during rotation because the second axis 86 is no longer aligned with the first axis 30 of the screw 12, the angled surface 102 on one or more of the blades 90 will engage the inner wall 66 of a respective slot 60, causing a reaction force which tends to self-correct the off-axis rotation. Thus, the engagement of the blades 90 on the driver 14 with the corresponding slots 60 in the head portion 40 of the screw 12 provides the apparatus 10 with the ability to retain the screw on the driver throughout the driving process.

Another advantageous feature of the present invention is the ability of the head portion 40 of the screw 12 to accept a conventional flat-head driver (not shown) in the event that a surgeon does not have the driver 14. This circumstance could occur, for example, if the bone screw 12 is being removed during a subsequent surgery by a different surgeon who is unaware of the design of the head portion 40 or does not have access to the driver 14. Both of the first and second grooves 70 and 72 in the head portion 40 can receive a flat-head screwdriver for rotating of the screw 12.

From the above description of the invention, those skilled in the art will perceive improvements, changes and modifications. For example, it should be understood that the bone screw 12 could have more or less than four slots 60, and that the associated driver 14 would have a corresponding number of blades 90. Such improvements, changes and modifications within the skill of the art are intended to be covered by the appended claims.

Having described the invention, we claim:

1. An apparatus for attaching to bone, said apparatus comprising:

a one-piece, homogeneous screw engageable by a driver for driving of said screw into bone, said screw having a shaft portion and a head portion extending from said shaft portion;

said shaft portion having an outer surface with a self-drilling thread convolution;

said head portion including oppositely disposed first and second axial ends and a peripheral surface extending between said axial ends, said first axial end adjoining said shaft portion, said second axial end including an end surface;

said head portion having a plurality of slots extending axially from said end surface to said first axial end, said plurality of slots further extending through said peripheral surface of said head portion and radially inward from said peripheral surface of said head portion; and a driver for driving said screw into bone, said driver having a main body portion and an end section, said end section having a plurality of blades projecting axially from said end section, each of said plurality of blades being adapted for receipt in and to drivingly engage a respective one of said slots in said head portion of said screw;

each of said plurality of blades having a peripheral surface that corresponds to at least a portion of said peripheral surface on said head portion of said bone screw so that said blades do not project radially or axially out of said slots;

at least two of said blades on said driver including tapering surfaces which engage a respective two of said slots on said head portion of said screw and wedge said screw onto said end section of said driver to prevent disengagement of said screw from said driver.

2. An apparatus for attaching to bone, said apparatus comprising:

a one-piece, homogeneous screw having a shaft portion and a head portion exiting from said shaft portion, said shaft portion having an outer surface with a thread convolution, said head portion including oppositely disposed first and second axial ends and a peripheral surface extending between said axial ends, said first axial end adjoining said shaft portion, said second axial end including an end surface;

said head portion having a plurality of slots extending axially from said end surface to said first axial end, said plurality of slots further extending through said peripheral surface of said head portion and radially inward from said peripheral surface of said head portion; and a driver for driving said screw into bone, said driver having an end section, said end section having a plurality of blades projecting axially from said end section;

each of said plurality of blades being adapted for receipt in and to drivingly engage a respective one of said slots in said head portion of said screw, each of said blades having a peripheral surface that corresponds to the shape of said peripheral surface on said head portion of said bone screw;

said head portion of said screw having four slots spaced 90° apart and said end portion of said driver having four blades spaced 90° apart;

said head portion of said screw further including intersecting first and second grooves formed in said end surface, said first groove extending radially between a diametrically opposed first pair of said slots and said second groove extending between a diametrically opposed second pair of said slots;

at least two of said blades on said driver including tapering surfaces which engage a respective two of said slots on said head portion of said screw and wedge said screw onto said end section of said driver to prevent disengagement of said screw from said driver.

3. The apparatus of claim 2 wherein said thread convolution on said shaft portion of said screw comprises self-drilling threads.

4. The apparatus of claim 2 wherein said thread convolution on said shaft portion of said screw comprises self-tapping threads.

5. An apparatus for attaching to bone, said apparatus comprising:

a one-piece, homogeneous screw having a shaft portion and a head portion exiting from said shaft portion, said shaft portion having an outer surface with a thread convolution, said head portion including oppositely disposed first and second axial ends and a peripheral surface extending between said axial ends, said first axial end adjoining said shaft portion, said second axial end including an end surface;

said head portion having a plurality of slots extending axially from said end surface to said first axial end, said plurality of slots further extending through said peripheral surface of said head portion an d radially inward from said peripheral surface of said head portion; and a driver for driving said screw into bone, said driver having an end section, said end section having a plurality of blades projecting axially from said end section;

each of said plurality of blades being adapted for receipt in and to drivingly engage a respective one of said slots in said head portion of said screw, each of said blades having a peripheral surface that corresponds to the shape of said peripheral surface on said head portion of said bone screw;

at least two of said plurality of blades on said driver include tapering surfaces which engage a respective two of said plurality of slots on said head portion of said screw and wedge said screw onto said end section of said driver to prevent disengagement of said screw from said driver.

6. The apparatus of claim 5 wherein said head portion of said screw has four slots spaced 90° apart and said end portion of said driver has four blades spaced 90° apart.

7. The apparatus of claim 5 wherein said peripheral surface of said head portion includes a cylindrical first surface portion, a conical second surface portion extending from said first surface portion to said shaft portion of said screw, and a tapered third surface portion extending from said first surface portion to said end surface of said head portion.

8. The apparatus of claim 5 wherein each of said plurality of blades has a peripheral surface that corresponds to at least a portion of said peripheral surface on said head portion of said bone screw so that said blades do not project out of said slots.

9. The apparatus of claim 5 wherein each of said plurality of blades has a peripheral surface which includes a cylindrical first surface and a conical second surface.

10. The apparatus of claim 5 wherein said head portion of said screw further includes intersecting first and second grooves formed in said end surface, said first groove extending radially between a diametrically opposed first pair of said slots and said second groove extending between a diametrically opposed second pair of said slots.

11. An apparatus for attaching to bone, said apparatus comprising:

a one-piece, homogeneous screw having a shaft portion and a head portion exiting from said shaft portion, said shaft portion having an outer surface with a thread convolution, said head portion including oppositely disposed first and second axial ends and a peripheral surface extending between said axial ends, said first axial end adjoining said shaft portion, said second axial end including an end surface;

said head portion having a plurality of slots extending axially from said end surface to said first axial end, said plurality of slots further extending through said peripheral surface of said head portion and radially inward from said peripheral surface of said head portion;

each of said plurality of slots being defined by a pair of side walls and an inner wall that is a segment of a frustum; and a driver for driving said screw into bone, said driver having an end section, said end section having a plurality of blades projecting axially from said end section;

each of said plurality of blades being adapted for receipt in and to drivingly engage a respective one of said slots in said head portion of said screw, each of said blades having a peripheral surface that corresponds to the shape of said peripheral surface on said head portion of said bone screw;

each of said plurality of blades including an angled surface for engaging said inner wall of each of said plurality of slots to cause a reaction force for correcting off-axis rotation of said driver relative to said screw.

12. The apparatus of claim 11 wherein said head portion of said screw has four slots spaced 90° apart and said end portion of said driver has four blades spaced 90° apart.

13. The apparatus of claim 11 wherein said peripheral surface of said head portion includes a cylindrical first surface portion, a conical second surface portion extending from said first surface portion to said shaft portion of said screw, and a tapered third surface portion extending from said first surface portion to said end surface of said head portion.

14. The apparatus of claim 13 wherein each of said plurality of blades has a peripheral surface that corresponds to at least a portion of said peripheral surface on said head portion of said bone screw so that said blades do not project out of said slots.

15. The apparatus of claim 13 wherein each of said plurality of blades has a peripheral surface which includes a cylindrical first surface and a conical second surface.

16. The apparatus of claim 15 wherein, when said blades of said driver are inserted into said slots in head portion of said screw, said first surface on each of said blades lies flush with said first surface portion of said peripheral surface of said head portion and said second surface on each of said blades lies flush with said second surface portion of said peripheral surface of said head portion.

17. The apparatus of claim 11 wherein said head portion of said screw further includes intersecting first and second grooves formed in said end surface, said first groove extending radially between a diametrically opposed first pair of said slots and said second groove extending between a diametrically opposed second pair of said slots.

18. The apparatus of claim 11 wherein at least two of said blades on said driver include tapering surfaces which engage a respective two of said slots on said head portion of said screw and wedge said screw onto said end section of said driver to prevent disengagement of said screw from said driver.

* * * * *